(12) United States Patent
Ono et al.

(10) Patent No.: US 8,088,624 B2
(45) Date of Patent: Jan. 3, 2012

(54) METHOD OF DETECTING THROMBOSIS BY MEASURING VON WILLENBRAND FACTOR-CLEAVING PROTEASE

(75) Inventors: Tomoko Ono, Tokyo (JP); Kenji Soejima, Kumamoto (JP); Masaki Hirashima, Kumamoto (JP); Wataru Morikawa, Kumamoto (JP); Yoichi Sakata, Tochigi (JP)

(73) Assignee: Mitsubishi Kagaku Iatron, Inc. (JP)

( * ) Notice: Subject to any disclaimer, the term of this patent is extended or adjusted under 35 U.S.C. 154(b) by 706 days.

(21) Appl. No.: 10/584,425

(22) PCT Filed: Dec. 22, 2004

(86) PCT No.: PCT/JP2004/019226
§ 371 (c)(1),
(2), (4) Date: May 30, 2007

(87) PCT Pub. No.: WO2005/062054
PCT Pub. Date: Jul. 7, 2005

(65) Prior Publication Data
US 2007/0275414 A1 Nov. 29, 2007

(30) Foreign Application Priority Data

Dec. 22, 2003 (JP) .................................. 2003-425706

(51) Int. Cl.
*G01N 33/86* (2006.01)
*G01N 33/53* (2006.01)
*G01N 33/00* (2006.01)

(52) U.S. Cl. .............. 436/69; 435/6; 435/7.1; 435/7.92; 435/7.94; 436/548; 436/16; 436/811

(58) Field of Classification Search ............... 435/4, 7.1, 435/7.92, 6, 7.94; 436/506, 518, 548, 16, 436/69, 177, 811
See application file for complete search history.

(56) References Cited

U.S. PATENT DOCUMENTS

2004/0214346 A1* 10/2004 Scheiflinger et al. .......... 436/518
2009/0220990 A1* 9/2009 Igami et al. .................... 435/7.4

FOREIGN PATENT DOCUMENTS

| EP | 1 391 516 | | 2/2004 |
| EP | 1 544 293 | | 6/2005 |
| EP | 1 544 293 | * | 6/2006 |
| JP | 4-029931 | | 5/1990 |
| WO | WO 02/42441 | | 5/2002 |

(Continued)

OTHER PUBLICATIONS

Konetschny et al. Development of a Highly Sensitive and Specific Enzyme-linked Immunosorbent Assay for the Detection of ADAMTS-13 in Human Plasma, Blood 102 (11) Abstract #4062 (Nov. 16, 2003).*

(Continued)

*Primary Examiner* — Gail R Gabel
(74) *Attorney, Agent, or Firm* — Brian E. Reese; Heslin Rothenberg Farley & Mesiti P.C.

(57) ABSTRACT

A method of detecting thrombosis or the degree of thrombophilia by measuring a von Willebrand factor cleaving protease, and a kit for detecting thrombosis or the degree of thrombophilia, comprising an antibody or a fragment thereof specifically binding to a von Willebrand factor-cleaving protease, are disclosed. The detection method and the detection kit have an excellent convenience, rapidity, and specificity.

5 Claims, 5 Drawing Sheets

FOREIGN PATENT DOCUMENTS

| WO | WO 03/016492 A | 2/2003 |
|---|---|---|
| WO | WO 2004/095027 | 11/2004 |

OTHER PUBLICATIONS

Strongin, Sensitivity, Specificity, and Predictive Value of Diagnostic Tests: Definitions and Clinical Applications, Laboratory Diagnosis of Viral Infections, Lennette, E. ed., Marcel Dekker Inc., New York, pp. 211-219 (1993).*

Furlan, M., et al., "Partial Purification and Characterization of a Protease From Human Plasma Cleaving von Willebrand Factor to Fragments Produced by In Vivo Proteolysis", Blood, vol. 87, pp. 4223-4234 (1996).

Gerritsen, H., "Partial Amino acid sequence of purified von Willebrand factor-cleaving protease", Blood, vol. 98, pp. 1654-1661 (2001).

Fujikawa, K., et al., Purification of human von Willebrand factor-cleaving protease an its identification as a new member of the metalloproteinase family, Blood, vol. 98, pp. 1662-1666 (2001).

Zheng, X., et al., "Structure of von Willebrand factor-cleaving protease (ADAMTSl3), a Metalloprotease involved in thrombotic thrombocytopenic Purpura", The Jrnl. of Biological Chem., vol. 276, pp. 41059-41063 (2001).

Soejima, K., et al., "A Novel Human Metalloprotease Synthesized in the Liver and Secreted into the Blood: Possibly, the von Willebrand Factor-Cleaving Protease?" The Jrnl. of Biological Chem., vol. 130, pp. 475-480 (2001).

Levy, C.G., et al., "Mutations in a member of the ADAMTS gene family cause thrombotic thrombocytopenic purpura", Nature, United Kingdom, vol. 413, pp. 488-494 (2001).

Kokame, K., et al., "VWF73, a region from D1596 to R1668 of von Willebrand factor, provides a minimal substrate for ADAMTS-13", Blood, vol. 103, pp. 607-612, (2004).

Veyradier et al. "Specific von Willebrand factor-cleaving pretease in thrombotic microagniopathies: a study of 111 cases." Blood, vol. 98, No. 6, pp. 1765-1772 (Sep. 2001).

Office Action issued on Jun. 8, 2011in connection with corresponding Canadian Patent Application No. 2,550,939.

Konetschny C, et al., "Development of a Highly Sensitive and Specific Enzyme-Linked Immunosorbent Assay for the Detection of ADAMTS-13 in Human Plasma", Blood, W.B. Saunders Company, vol. 102, No. 11, Nov. 16, 2003, p. 89b.

Obert B, et al., "Estimation of The Von Willebrand Factor-Cleaving Protease in Plasma Using Monoclonal Antibodies to VWF" Thrombosis and Haemostasis, Stuttgart, vol. 82, No. 5, Nov. 1999.

Kokame K, et al., "Mutations and common polymorphisms in ADAMTS13 gene responsible for van Willebrand factor-cleaving protease activity", Proceedings of the National Academy of Sciences of USA, National Academy of Science, vol. 99, No. 18, Sep. 3, 2002, pp. 11902-11907.

Supplementary Search Report for EP04807583, Sep. 2007.

* cited by examiner

METHOD OF DETECTING THROMBOSIS BY MEASURING VON WILLENBRAND FACTOR-CLEAVING PROTEASE

CROSS REFERENCE TO RELATED APPLICATIONS

This application is a 35 U.S.C. §371 U.S. national stage filing from PCT Application Ser. No. PCT/JP2004/019226 having an international filing date of Dec. 22, 2004, published under WO 2005/062054 A1 on Jul. 7, 2005, which claims priority to Japanese Application Serial Number 2003-425706, filed Dec. 22, 2003. The disclosures of these applications are incorporated by reference in their entirety into the current application.

TECHNICAL FIELD

The present invention relates to a method and a kit for detecting thrombosis or the degree or severity of thrombophilia on the basis of measuring a von Willebrand factor cleaving protease. The present invention can be carried out by using an immunological method with a monoclonal antibody and/or a polyclonal antibody against the von Willebrand factor cleaving protease.

BACKGROUND ART

When a blood vessel wall is damaged and subendothelial tissue is exposed to blood flow, platelets in the blood flow rapidly adhere to the subendothelial tissue. The adhesion requires a human von Willebrand factor (hereinafter simply referred to as "vWF") in plasma. The vWF triggers a series of platelet activation steps, such as platelet aggregation and a release of intracellular granules, and then, formed thrombi lead hemostasis. In general, the vWF is secreted from a vascular endothelium to blood as a macromolecule having a molecular weight of more than 20,000 kDa, and cleaved by a metalloprotease, vWF-cleaving protease, into multimers having molecular weights of 500 to 20,000 kDa, which circulate through the blood. When a disease occurs (i.e., when a high shear stress is caused by occlusion or the like), the conformation of the vWF changes to an expanded structure. It is known that the expanded vWF has a high platelet aggregation activity, and the expanded vWF is liable to be degraded by the vWF-cleaving protease. It is considered that when the enzyme activity is lowered for some reason, "unusually large" vWF molecules are overproduced in the blood and efficiently bind to platelets and, as a result, the platelet aggregation in blood vessels is promoted to form thrombi in microcirculation. Such thrombus formation involved in platelets is essential for physiological hemostatic mechanisms. However, thrombi cause thrombotic diseases (such as cardiac infarction, cerebral infarction, or cerebral thrombosis), which are a major cause of death and a serious problem in an aging society.

It has been clarified that the vWF-cleaving protease is involved in thrombotic thrombocytopenic purpura (hereinafter simply referred to as "TTP") which is extremely severe and has a high degree of fatality, that an autoantibody which inhibits the vWF-cleaving protease activity is produced in acute and sporadic TTP, and that the vWF-cleaving protease activity is inactive in familial TTP. Although a part of the vWF-cleaving protease was purified in 1996 (non-patent reference 1), the whole thereof was not identified until 2001. Because the vWF-cleaving protease exhibits its enzyme activity only in the presence of 1.5 mol/L urea/5 mmol/L Tris buffer (pH 8.0) in vitro, it was difficult to identify the vWF-cleaving protease as a substance. Recently, the plasma vWF-cleaving protease was purified (non-patent references 2 and 3). Further, cDNA thereof was cloned, and the gene, which belongs to an ADAMTS (a disintegrin like and metalloprotease with thrombospondin type 1 motif) family, was named ADAMTS13 (non-patent references 4 and 5). In the same period of time, it was clarified that the vWF-cleaving protease activity was significantly lowered in familiar TTP, due to a mutation of the vWF-cleaving protease gene ADAMTS13 (non-patent reference 6).

The vWF-cleaving protease activity was measured by detecting the large vWF multimers, using a combination of an SDS-agarose electrophoresis and autoradiography or Western blotting (non-patent reference 1). However, this measuring method contains complicated steps, and thus, is not a commonly used clinical laboratory test. For example, in this measuring method, a protease-free vWF is required, the procedure takes 3 days, and the measured values often vary in accordance with laboratories.

Recently, a method of measuring the vWF-cleaving protease activity, comprising the steps of expressing a partial region of an A2 domain (a site to be cleaved by the vWF-cleaving protease) of the vWF in *Escherichia coli* using genetic recombination techniques, mixing the recombinant protein with a sample derived from a patient for a predetermined period, to cleave the A2 domain by the vWF-cleaving protease contained in the sample, and detecting the cleaved products by a combination of SDS electrophoresis and Western blotting, was developed (non-patent reference 7). However, this method also contains complicated steps, such as a preparation of the recombinant protein or electrophoresis, and thus, it is difficult to use this method in most laboratories.

Idiopathic thrombocytopenic purpura (ITP) is a disease in which characteristic symptoms and clear causes of disease are unknown, and thrombocytopenia occurs by platelet destruction promoted by immunological mechanisms. In most cases, ITP is considered an autoimmune disease caused by an autoantibody against a platelet. As an antigen recognized by an anti-platelet antibody derived from a patient suffering from ITP, a platelet membrane protein GPIIb-IIIa was identified, and many methods for detecting an antibody specific for this protein were developed. Among these methods, an antigen capture assay using a monoclonal antibody against GPIIb-IIIa is widely used. It is known that this method shows a high specificity with a little false positive. However, most monoclonal antibodies which may be used in this method are not commercially available, and complicated steps, such as a collection of platelets or a dissolution of platelets, are required, and thus, the development of a convenient kit and standardization are required.

DISCLOSURE OF THE INVENTION

Problems to be Solved by the Invention

As described above, a method for conveniently and accurately detecting causes of thrombosis involved in platelet aggregation and/or thrombosis was not established, and such a method has been desired.

Therefore, an object of the present invention is to establish such a desired method for detecting the degree of thrombophilia in thrombosis involved in platelet aggregation. The detection method may be used as a diagnosis method which targets a novel treatment of thrombosis, such as an increased survival rate or a determination of treatment on the basis of symptoms. The present inventors conducted intensive studies and, as a result, found that the concentration of the vWF-cleaving protease in plasma derived from patients suffering from thrombosis was significantly lowered, in comparison with healthy people, on the basis of the results obtained by an enzyme-linked immunosorbent assay using monoclonal or polyclonal antibodies against the vWF-cleaving protease, and the present invention was completed.

Means for Solving the Problems

The problem may be solved by the present invention, i.e., a method of detecting thrombosis or the degree of thrombophilia, characterized by measuring a von Willebrand factor-cleaving protease.

According to a preferred embodiment of the detection method of the present invention, thrombosis is selected from the group consisting of acute or chronic myeloid leukemia, acute promyelocytic leukemia, systemic lupus erythematosus, pulmonary embolism, cerebral infarction, veno-occlusive disease, acute lymphocytic leukemia, thrombotic microangiopathy, thrombotic thrombocytopenic purpura, hemolytic uremic syndrome, and deep vein thrombosis.

According to another preferred embodiment of the detection method of the present invention, the degree of thrombophilia is detected in a patient under a long-term treatment with dialysis accompanied by repeated shunt.

According to still another preferred embodiment of the detection method of the present invention, a decreased concentration of the von Willebrand factor-cleaving protease for a patient with such a disease is used as an index, in comparison with the concentration of that for healthy people.

According to still another preferred embodiment of the detection method of the present invention, the von Willebrand factor-cleaving protease is immunologically measured using at least an antibody which specifically binds to the von Willebrand factor-cleaving protease, or a fragment of the antibody.

The present invention relates to a kit for detecting thrombosis or the degree of thrombophilia, characterized by comprising an antibody which specifically binds to a von Willebrand factor-cleaving protease, or a fragment of the antibody.

The term "analysis" (for example, an analysis of an autoantibody) as used herein includes a detection to judge a presence or absence of a substance (for example, an autoantibody) to be analyzed, and a measurement to quantitatively or semi-quantitatively determine an amount of a substance to be analyzed.

Effects of the Invention

The present invention enables a detection of the degree of a thrombophilia in a patient suffering from a disease leading to thrombosis, such as pulmonary embolism, cerebral thrombosis, or leukemia, and is clinically valuable.

According to the method of the present invention, thrombosis or the degree of thrombophilia can be diagnosed conveniently, rapidly, and specifically.

In particular, when the vWF-cleaving protease is immunologically measured, the measurement can be carried out for 3 to 4 hours with good reproducibility, whereas a conventional method measuring the protease activity using electrophoresis takes 3 days, and measured values often vary in accordance with, for example, the analysts or reagents.

BEST MODE FOR CARRYING OUT THE INVENTION

[1] Detection Method of the Present Invention

In the detection method of the present invention, the degree of thrombophilia can be evaluated, and a presence or absence of thrombosis can be judged, by measuring a concentration of the von Willebrand factor-cleaving protease (vWF-cleaving protease) and comparing the measured concentration with that of healthy people.

The term "von Willebrand factor-cleaving protease" as used herein means a metalloprotease, sometimes referred to as ADAMTS13, which specifically cleaves the von Willebrand factor (vWF) at the bond between tyrosine (842) and methionine (843) contained in an A2 domain thereof.

As shown in Example 2 below, a concentration of the vWF-cleaving protease contained in each body fluid sample collected from patients suffering from thrombosis involved in platelet aggregation is significantly decreased, in comparison with healthy people. Therefore, in the detection method of the present invention, when a measured concentration of the vWF-cleaving protease in a subject to be judged is lower than that in healthy people, the subject can be diagnosed as having thrombosis.

The term "thrombosis" as used herein includes, for example, acute myeloid leukemia (AML), chronic myeloid leukemia (CML), acute promyelocytic leukemia (APL), systemic lupus erythematosus (SLE), pulmonary embolism, cerebral infarction, veno-occlusive disease (VOD), acute lymphocytic leukemia (ALL), thrombotic microangiopathy (TMA), and deep vein thrombosis (DVT). Typical diseases of thrombotic microangiopathy (TMA) include, for example, thrombotic thrombocytopenic purpura (TTP) and hemolytic uremic syndrome (HUS).

TTP is a severe disease characterized by pentad, that is, (1) thrombocytopenia, (2) microangiopathic hemolytic anemia, (3) renal failures, (4) fever, and (5) neurologic disturbances. HUS is a severe disease characterized by triad, that is, (1) thrombocytopenia, (2) microangiopathic hemolytic anemia, and (3) renal failures. TTP and HUS are regarded as a common pathosis, TMA, in view of similarities in clinical pictures, and clinically distinguished on the basis of the presence or absence of (5) neurologic disturbances and the presence or absence of severe renal failures. Recently, a method of measuring the vWF-cleaving protease activity and its inhibitor titer has been established, and can be used to distinguish TTP from HUS.

Further, as shown in Example 3 described below, in comparison with a group of patients not operating shunt, the amount of vWF-cleaving protease in a group of patients operating repeated shunt was significantly lowered, and the result correlated to the fact that patients operating repeated shunt showed remarkable thrombophilia. Further, after 2 hours from the beginning of dialysis, the amount of vWF-cleaving protease was significantly lowered, in comparison with that after the completion of dialysis, and the result accorded with clinical observations of thrombophilia and a clogging tendancy of shunt during dialysis. These results indicate that a decreased amount of the vWF-cleaving protease correlates to an increased severity of thrombophilia. Therefore, in the detection method of the present invention, when a measured concentration of the vWF-cleaving protease in a subject to be judged is lower than that in healthy people, it can be judged that the subject shows remarkable thrombophilia.

"State in which the concentration of the vWF-cleaving protease is low" as used herein includes not only a state in which the absolute amount of the vWF-cleaving protease is low, but also a state in which the apparent amount of the vWF-cleaving protease is low. For example, when an autoantibody against the vWF-cleaving protease exists, a complex of the vWF-cleaving protease and the autoantibody is formed, and thus, the apparent amount of the vWF-cleaving protease becomes low.

In the method of the present invention, a quantitative determination of the vWF-cleaving protease may be carried out, for example, by an immunological method or a biochemical method (such as an enzymological method), preferably by an immunoassay using a monoclonal and/or polyclonal antibody which specifically binds to the vWF-cleaving protease (hereinafter referred to as "anti-vWF-CP antibody"), or a fragment of the antibody.

As the antibody fragment, for example, Fab, Fab', F(ab')$_2$, or Fv may be used. Hereinafter, the method of the present invention will be further illustrated by embodiments using an antibody (i.e., an immunoglobulin molecule per se), but it is easy for those skilled in the art to replace the antibody with an antibody fragment, if desired.

In the method of the present invention, it is preferable to use two or more anti-vWF-CP antibodies having different specificities, more preferably a combination of an anti-vWF-CP monoclonal antibody (i.e., the first monoclonal antibody), and another anti-vWF-CP monoclonal antibody which binds to the vWF-cleaving protease at a region different from that recognized by the first monoclonal antibody (i.e., the second monoclonal antibody) or an anti-vWF-CP polyclonal antibody.

As the anti-vWF-CP monoclonal antibody, there may be mentioned, for example, mouse monoclonal antibodies WH10 (IgG1), WH2-22-1A (IgG1), WH63.1 (IgG1), WH7-2B (IgG1), WH14-3 (IgG1), or WH50-3 (IgG1). It is preferable that at least one of anti-vWF-CP monoclonal antibodies is of the mouse monoclonal antibodies WH10 (IgG1), WH2-22-1A (IgG1), and WH63.1 (IgG1). The preferable first monoclonal antibody is the antibody WH10, and the preferable second monoclonal antibody is the antibody WH2-22-1A or WH63.1.

The mouse monoclonal antibodies WH10, WH2-22-1A, and WH63.1 are produced by hybridomas WH10, WH2-22-1A, and WH63.1, respectively.

The hybridomas WH10 and WH63.1 were internationally deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Sep. 4, 2002, and the international deposit numbers are FERM BP-8174 and FERM BP-8175, respectively.

The hybridoma WH2-22-1A was domestically deposited in the International Patent Organism Depositary National Institute of Advanced Industrial Science and Technology on Apr. 22, 2003, and was transferred to an international deposit on Sep. 12, 2003. The international deposit number (a number in parenthesis [ ] following the international deposit number is a domestic deposit number) is FERM BP-08483 [FERM P-19324].

Monoclonal or polyclonal antibodies used in the present invention may be prepared by conventional methods, except that the vWF-cleaving protease is used as an immunogen. The above monoclonal antibodies WH7-2B, WH14-3, and WH50-3, which have not been deposited but may be used in the present invention, were prepared in a similar fashion.

When an immunoassay is used in the method of the present invention, the assay may be carried out in accordance with, for example, a commonly-used enzyme-linked immunosorbent assay (ELISA) using a sandwich method, or a commonly-used agglutination method or an RIA method using a sandwich method or a competition method. Each method may be carried out in accordance with a conventional method.

It is preferable that the method of the present invention is carried out by a two-step sandwich method using anti-vWF-CP monoclonal antibodies. The two-step sandwich method may be carried out, for example, in accordance with the following procedures.

In a preferred embodiment, an anti-vWF-CP monoclonal antibody immobilized on an appropriate carrier (such as a 96-well plate) is used as the first antibody. The immobilized first monoclonal antibody is reacted with a sample to be assayed (such as an experimental sample) containing a substance to be measured (i.e., the vWF-cleaving protease), or a standard solution containing the vWF-cleaving protease, at room temperature for 2 hours [the first step]. The second anti-vWF-CP antibody (such as a mouse anti-vWF-CP monoclonal antibody) labeled with an enzyme is added to the plate, and allowed to stand at room temperature for about 1 hour, to react the second antibody with a reaction product (i.e., a complex of the first monoclonal antibody and the substance to be measured) obtained in the first step [the second step]. Coloring reagents are added to start a coloring reaction, and 0.5 N sulfuric acid is added to stop the reaction. And then, an absorbance at 450 nm is measured.

In another preferred embodiment, after the first step, an anti-vWF-CP rabbit serum (i.e., rabbit anti-vWF-CP polyclonal antibody) as the second antibody is added to the plate, and allowed to stand at room temperature for about 1 hour, to react the second antibody with a reaction product (i.e., a complex of the monoclonal antibody and the substance to be measured) obtained in the first step. If desired, a certain amount of a labeled antibody (such as a labeled anti-rabbit-IgG antibody) may be added to the plate, and allowed to stand at room temperature for about 1 hour. As described above, the vWF-cleaving protease contained in a sample to be assayed can be measured.

In the method of the present invention, each antibody may be immobilized (i.e., insolubilized) by physically or chemically binding to an insoluble carrier, in accordance with conventional methods. As the carrier for insolubilization, for example, polystyrene, Sephadex, ion-exchange resins, a plastic tube, or amino copolymers may be used. The solubilization may be carried out by, for example, a covalent binding method (such as a diazo method, a peptide method, or an alkylation method), a carrier binding method using a crosslinking reagent, an ionic binding method using a carrier such as ion-exchange resins, or a physical adsorption method using porous glass such as glass beads as a carrier.

The polyclonal antibody used in the present invention is not particularly limited, so long as it recognizes the vWF-cleaving protease. As the polyclonal antibody, an antiserum produced in a living body by administering, to a mammal, the same antigen as that used in preparing the above-mentioned monoclonal antibody may be used. The antiserum may be collected from a mammal in accordance with a conventional method.

As the labeled antibody used for labeling, various known labeled antibodies may be used. Such a labeled antibody may be prepared, for example, by labeling a commercially available antiserum (i.e., anti-immunoglobulin antibody), which is obtained from an immunized animal (for example, a mouse, a rat, a guinea pig, a rabbit, a sheep, a goat, a horse, or cattle), with an appropriate enzyme [for example, a peroxidase (POD), an alkaline phosphatase, a β-D-galactosidase, or an acidic phosphatase] in accordance with a conventional method. As the labeled antibody, for example, a POD-labeled anti-rabbit-IgG antibody or a POD-labeled anti-mouse-IgG antibody may be used.

A preferred sample to be assayed by the method of the present invention is, for example, blood plasma. As samples other than the plasma, there may be mentioned, for example, various body fluids, such as cell or tissue fluids, lymph, a thymic fluid, a ascites fluid, an amniotic fluid, gastric juices, urine, pancreatic juices, spinal fluid, or saliva. The plasma is preferably citrated plasma.

As a solution used in the measuring system, various solution which do not produce bad influence on the reaction may be used. As the solution, a buffer having a pH of approximately 5.0 to 9.0, such as a citrate buffer, a phosphate buffer, a Tris-HCl buffer, or a carbonate buffer, is preferable. It is preferable that the solvent contains an approximately 0.1 to 10 w/v % serum and/or approximately 0.1 to 1 M NaCl, in view of the object(s) in the method of the present invention.

In the method of the present invention, after the immunoreaction, a separation of solid phase-liquid phase (i.e., the complex of the reaction product and the labeled antibody—the unreacted labeled antibody in the two-step sandwich method) can be carried out by a conventional method, such as centrifugation, filtration, decantation, or washing.

An enzyme activity of the labeled substance separated as above may be measured by a known method in accordance with the kind of enzyme for labeling. As the coloring solution used in the measurement, a commonly-used substance may be used. For example, when a peroxidase is used as the enzyme for labeling, tetramethyl benzidine (TMB), o-phenylenediamine (OPD)], or the like may be used. The coloring reaction may be stopped in accordance with a conventional method, for example, by adding an appropriate inhibitor for the enzyme, such as 0.5 to 4 N sulfuric acid, to the reaction solution.

[2] Detection Kit of the Present Invention

The detection kit of the present invention contains at least an anti-vWF-CP antibody or a fragment thereof, and preferably contains two or more anti-vWF-CP antibodies having different specificities. The detection kit of the present invention may be used for the detection method of the present invention.

In the detection kit of the present invention, it is more preferable to use a combination of the first anti-vWF-CP monoclonal antibody, and another anti-vWF-CP monoclonal antibody which binds to the vWF-cleaving protease at a region different from that recognized by the first monoclonal antibody (i.e., the second monoclonal antibody) or the anti-vWF-CP polyclonal antibody.

The first antibody may be preferably immobilized on an appropriate carrier (i.e., a carrier for immobilization). The second antibody may be a labeled antibody. Alternatively, the kit may contain a labeled antibody against the second antibody, when the second antibody is not labeled.

A reagent containing the monoclonal antibody may contain a stabilizing agent, such as glycerol or bovine serum proteins. The antibody reagent may be in a liquid form or a lyophilized form. When the kit contains the antibody reagent in a lyophilized form, the kit may contain an aqueous solvent or a solvent miscible with water. Further, the antibody reagent may contain a buffer capable of maintaining a constant pH in a reconstituted reagent system, or a preservative to prevent deterioration. As the buffer, a buffer capable of maintaining a pH of approximately 5.0 to 9.0, when the method of the present invention is carried out, is preferable. A reconstituting agent preferably contains water. In the reconstituting agent, a part of water or the whole thereof may be replaced with a reagent miscible with water. As the reagent miscible with water, known reagents, such as glycerol, alcohols, or glycol ethers, may be used.

EXAMPLES

The present invention now will be further illustrated by, but is by no means limited to, the following Examples.

Example 1

Measurement of vWF-Cleaving Protease (a) Combinations of Monoclonal Antibodies: Sandwich Enzyme Immunoassay for vWF-Cleaving Protease Among 6 clones of anti-vWF-CP monoclonal antibodies (WH10, WH2-22-1A, WH63.1, WH7-2B, WH14-3, and WH50-3) obtained by using the vWF-cleaving protease as an immunogen, the most appropriate combination thereof was determined in accordance with the following procedure.

Each anti-vWF-CP monoclonal antibody was diluted to 2 µg/mL with a phosphate-buffered saline (PBS), and added to each well (100 µL per well) of a 96-well EIA plate (Nunc). The plate was allowed to stand at 4° C. overnight for coating. Unbound antibodies were removed by washing with PBS, and 250 µL of PBS supplemented with 2% bovine serum albumin (BSA) was added to each well. The plate was allowed to stand at 4° C. overnight for blocking. The blocking solution was removed by washing with PBS containing 0.1% Tween20 (PBST), and 100 µL of a sample (normal human pooled plasma) or a standard (prepared from a purified vWF-cleaving protease antigen) was added to each well. The reaction was carried out at room temperature for 2 hours. The reaction solution was removed by washing with PBST, and 100 µL of 1 µg/mL biotin-labeled anti-vWF-CP antibody was added to each well. The reaction was carried out at room temperature for 1 hour. The reaction buffer was removed by washing with PBST, and 100 µL of a 0.1 µg/mL of peroxidase-labeled streptavidin (BioRad) was added to each well. The reaction was carried out at room temperature for 1 hour. After washing, 100 µL of a tetramethyl benzidine (TMB)/hydrogen peroxide solution (KPL) was added to each well, and the reaction was carried out at room temperature for 15 minutes. An absorbance at 450 nm was measured using a microtiterplate reader.

As a result, any combination can be used for the measurement. Among all the combinations, a combination in which the monoclonal antibody WH10 was coated as the immobilized antibody and the monoclonal antibody WH2-22-1A or WH63.1 was used as the second antibody showed the most sensitivity.

(b) Labeling of Monoclonal Antibodies with Enzyme

The antibodies WH2-22-1A and WH63.1 were labeled with a peroxidase by a method of Imagawa et al. [Imagawa et al. (1982) J. Appl. Biochem., 4, 41]

(c) Sandwich Enzyme-Linked Immunosorbent Assay Using Monoclonal Antibodies

The measurement of the purified vWF-cleaving protease was carried out in accordance with the procedure described in Example 1(a), except for the following conditions. The anti-vWF-CP monoclonal antibody WH10 was coated on each well of a 96-well EIA plate (Nunc) at a concentration of 2 µg/mL. A normal human pooled plasma was used as a standard. The antibody WH2-22-1A or WH63.1 labeled with a peroxidase in Example 1(b) was used as the second antibody. The TMB/hydrogen peroxide solution (KPL) was used as a substrate solution. As a stopping solution, 0.5 N sulfuric acid was used. An absorbance at 450 nm was measured.

The result is shown in FIG. 1. The Y axis in FIG. 1 is an absorbance at 450 nm. When the normal human pooled plasma is defined as 1 Unit (U), the vWF-cleaving protease having an amount of 0.03 U or more could be accurately measured, as shown in FIG. 1.

(d) Combination of Monoclonal Antibody and Polyclonal Antibody: Sandwich Enzyme-Linked Immunosorbent Assay of vWF-Cleaving Protease The anti-vWF-CP monoclonal antibody WH10 was diluted to 2 µg/mL with PBS, and added to each well (100 µL per well) of a 96-well EIA plate (Nunc). The plate was allowed to stand at 4° C. overnight for coating. Unbound antibodies were removed by washing with PBS, and 250 µL of PBS supplemented with 25% Block Ace (Dainippon pharmaceutical) was added to each well. The plate was allowed to stand at room temperature for blocking. The blocking solution was removed by suction, and 100 µL of a normal human pooled plasma was added to each well. The reaction was carried out at room temperature for 2 hours. The reaction solution was removed by washing with PBST, and 100 µL of 0.5 µg/mL anti-vWF-CP polyclonal antibody was added to each well. The reaction was carried out at room temperature for 1 hour. The reaction solution was removed by washing with PBST, and 100 µL of a peroxidase-labeled anti-rabbit-IgG polyclonal antibody (BioRad) solution previously diluted to 10000-fold was added to each well. The reaction was carried out at room temperature for 1 hour. After washing, 100 µL of the TMB/hydrogen peroxide solution (KPL) was added to each well. The reaction was carried out at room temperature for 5 minutes, and 100 µL of 0.5 N sulfuric acid was added. An absorbance at 450 nm of each reaction solution was measured using a colorimeter for microtiterplate.

The result is shown in FIG. 1. The abbreviation "PoAb" described in FIG. 1 means the polyclonal antibody. When the normal human pooled plasma is defined as 1 U, the vWF-cleaving protease having an amount of 0.03 U or more could be accurately measured by the combination used in this example, as shown in FIG. 1.

Example 2

Comparison of vWF-Cleaving Protease Concentrations in Various Diseases

The plasma vWF-cleaving protease was measured by the sandwich enzyme-linked immunosorbent assay described in Example 1(c) or Example 1(d). In this measurement, a normal human pooled plasma was used as a standard, and is defined as 1 U.

The result obtained by the combination of antibodies WH10 and WH2-22-1A is shown in FIG. 2. The result obtained by the combination of antibodies WH10 and WH63.1 is shown in FIG. 3. The result obtained by the combination of antibody WH10 and the polyclonal antibody is shown in FIG. 4. The result obtained by comparing the amounts of vWF-cleaving protease in healthy people and patients suffering from various diseases is shown in Table 1.

The abbreviations "AML", "APL", "CML", "HUS", "TTP", "ALL", "SLE", and "DVT" described in FIGS. 2 to 4 and Table 1 mean acute myeloid leukemia, acute promyelocytic leukemia, chronic myeloid leukemia, hemolytic uremic syndrome, thrombotic thrombocytopenic purpura, acute lymphocytic leukemia, systemic lupus erythematosus, and deep vein thrombosis, respectively. The abbreviations "MEAN", "SEM", and "normal" described in Table 1 mean an average value, a standard error, and healthy people, respectively. The unit of the Y axis in FIGS. 2 to 4 is calculated from a calibration curve prepared on the basis of the results obtained from a diluted series of the normal human pooled plasma.

In comparison with the average concentration of the vWF-cleaving protease in the healthy people group (N=12), the average concentration of the vWF-cleaving protease in each patient group was significantly lowered, regardless of the combinations of antibodies. Further, it was confirmed that the concentration of the vWF-cleaving protease in patients suffering from a veno-occlusive disease (VOD) was lower than that in healthy people (data not shown).

TABLE 1

| a | b | normal N = 12 | AML 31 | APL 10 | CML 4 | TTP 7 | HUS 5 | ALL 11 | c 17 | d 18 | SLE 12 | DVT 7 |
|---|---|---|---|---|---|---|---|---|---|---|---|---|
| WH2-22-1A | MEAN | 1.027 | 0.555 | 0.431 | 0.597 | 0.356 | 0.375 | 0.616 | 0.711 | 0.659 | 0.611 | 0.584 |
|  | SEM | 0.028 | 0.110 | 0.029 | 0.005 | 0.005 | 0.036 | 0.147 | 0.104 | 0.069 | 0.052 | 0.074 |
|  | p < | — | 0.001 | 0.001 | 0.001 | 1E–07 | 0.001 | 0.010 | 0.002 | 0.001 | 0.001 | 0.001 |
| WH63 | MEAN | 1.095 | 0.585 | 0.623 | 0.439 | 0.325 | 0.387 | 0.471 | 0.657 | 0.573 | 0.617 | 0.543 |
|  | SEM | 0.205 | 0.219 | 0.184 | 0.012 | 0.025 | 0.036 | 0.073 | 0.145 | 0.131 | 0.032 | 0.039 |
|  | p < | — | 0.005 | 0.050 | 0.050 | 6E–05 | 0.001 | 0.001 | 0.050 | 0.005 | 0.005 | 0.010 |
| P0Ab | MEAN | 0.902 | 0.614 | 0.588 | 0.629 | 0.388 | 0.522 | 0.677 | 0.742 | 0.639 | 0.714 | 0.714 |
|  | SEM | 0.004 | 0.082 | 0.092 | 0.002 | 0.063 | 0.039 | 0.133 | 0.086 | 0.076 | 0.049 | 0.052 |
|  | p < | — | 0.001 | 0.010 | 0.001 | 9E–05 | 0.020 | 0.067 | 0.050 | 0.001 | 0.020 | 0.077 | a: Second antibody
b: Disease group
c: Pulmonary embolism
d: Cerebral infarction

Example 3

Changes of vWF-Cleaving Protease Before Dialysis, after Two Hours from the Beginning of Dialysis, and after the Completion of Dialysis, in Patients Under a Long-Term Treatment with Dialysis with or without Shunt Plasma samples were collected from patients under a long-term treatment with dialysis accompanied by repeated shunt, and patients under a long-term treatment with dialysis but not operating shunt. The plasma samples were used to measure the vWF-cleaving protease by the sandwich enzyme-linked immunosorbent assay using the combination of antibodies WH10 and WH2-22-1A described in Example 1(c). The result is shown in FIG. 5. The unit of the Y axis in FIG. 5 is calculated from a calibration curve prepared on the basis of the results obtained from a diluted series of the normal human pooled plasma. The abbreviation "PLT<10^5"" described in FIG. 5 means that the number of platelets was less than $1 \times 10^5 / \mu L$.

In comparison with the group of patients not operating shunt, the amount of vWF-cleaving protease in the group of patients operating repeated shunt was significantly lowered, and the result correlated to the fact that patients operating repeated shunt showed remarkable thrombophilia. Further, after 2 hours from the beginning of dialysis, the amount of vWF-cleaving protease was significantly lowered, in comparison with that after the completion of dialysis, and the result accorded with clinical observations of a thrombophilia and clogging tendency of shunt during dialysis.

As described above, according to the method of the present invention, the degree of thrombosis can be detected in a patient suffering from diseases leading to thrombosis. Further, according to the method of the present invention, the degree of thrombophilia after dialysis can be monitored easily in a patient under a long-term treatment with dialysis accompanied by repeated shunt. Furthermore, the method of the present invention shows the possibilities of a prediction of shunt occlusion or an observation of prognosis.

INDUSTRIAL APPLICABILITY

According to the present invention, thrombosis or the degree of thrombophilia can be detected.

Although the present invention has been described with reference to specific embodiments, various changes and modifications obvious to those skilled in the art are possible without departing from the scope of the appended claims.

Figure 1:
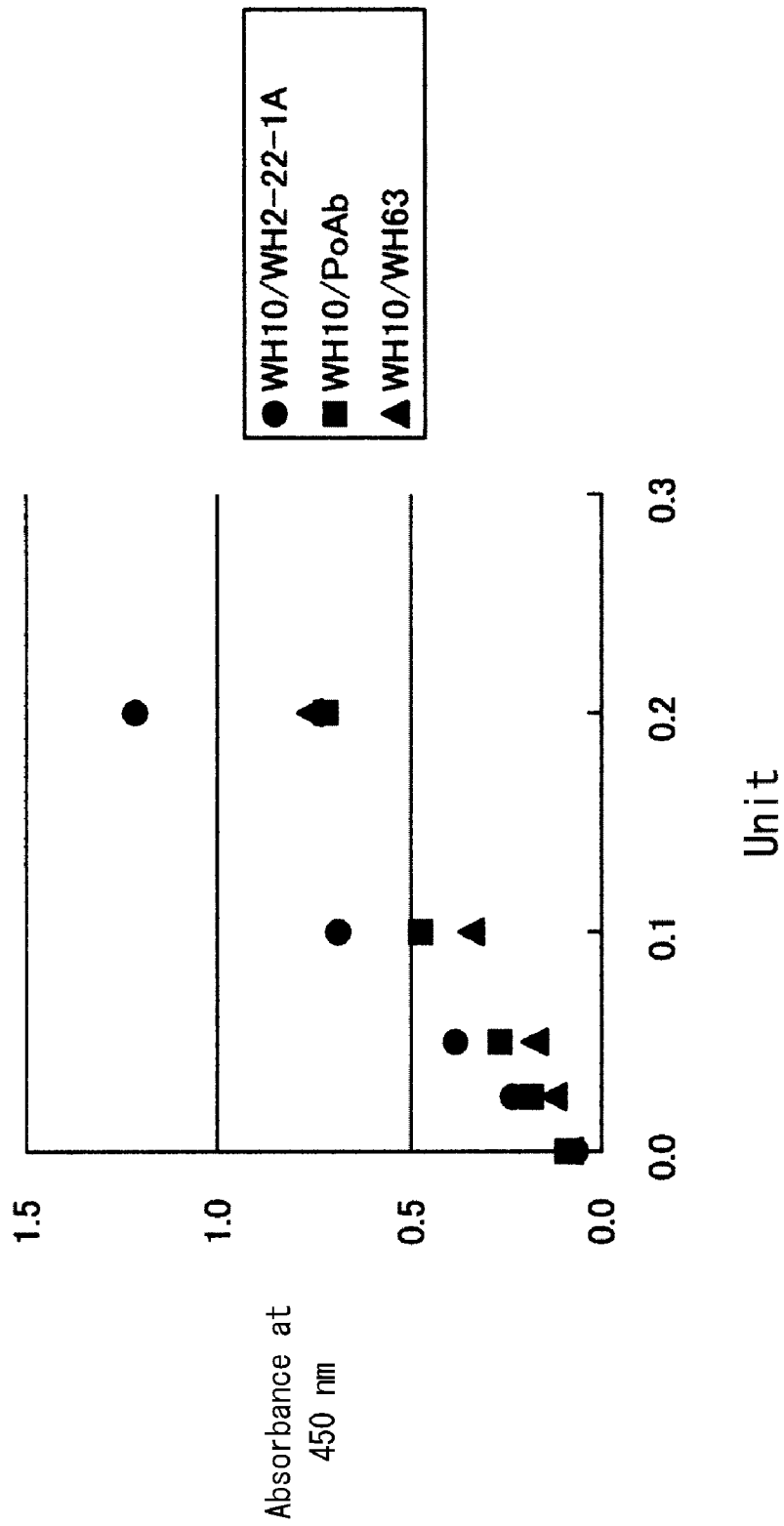
FIG. 1 is a graph showing calibration curves obtained by using combinations of monoclonal antibodies or a combination of a monoclonal antibody and a polyclonal antibody.
Figure 2:
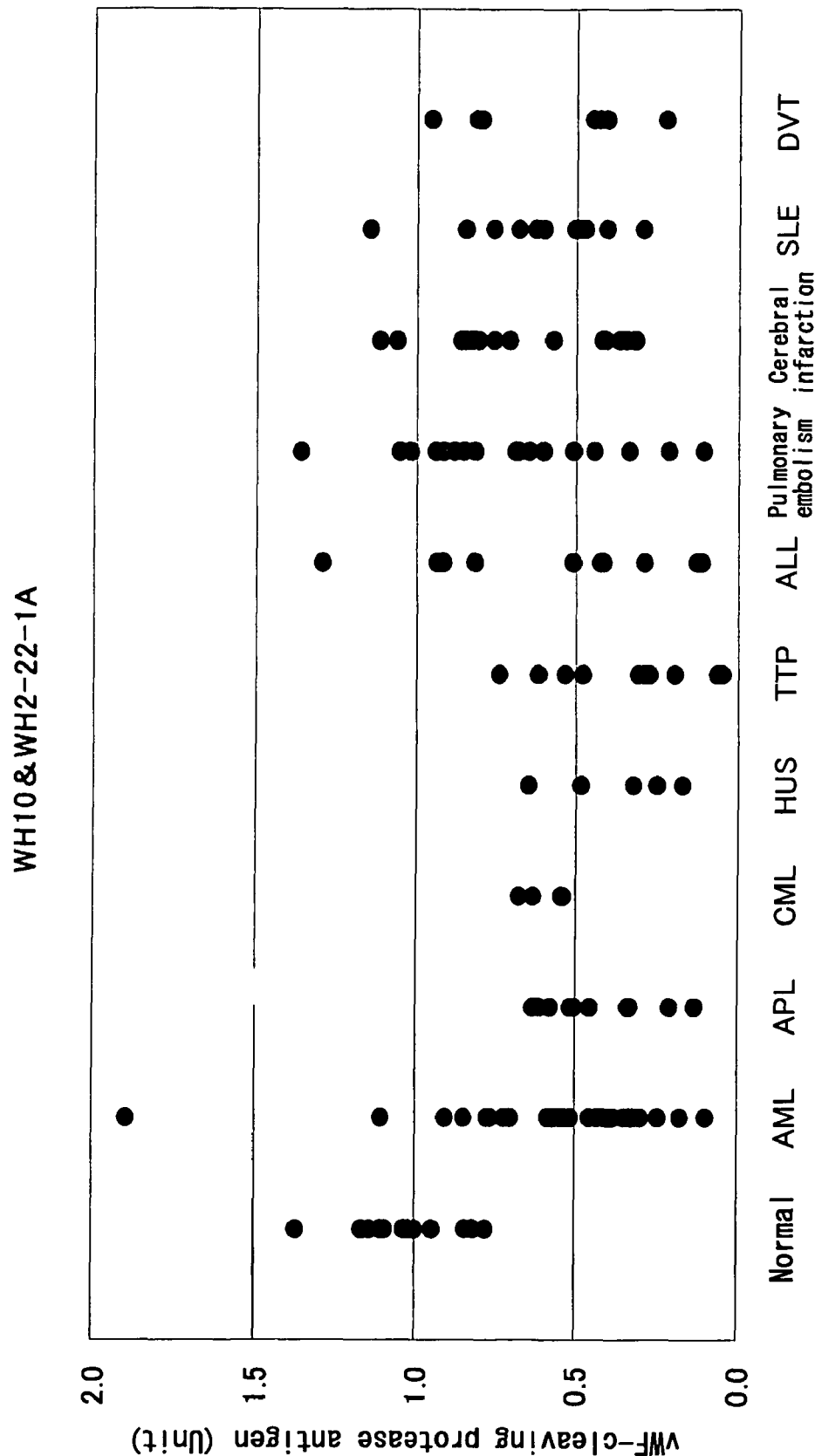
FIG. 2 is a graph showing the result obtained by comparing the amounts of vWF-cleaving protease in healthy people and patients suffering from various diseases, on the basis of the measurement using the combination of monoclonal antibodies WH10 and WH2-22-1A which specifically bind to the vWF-cleaving protease.
Figure 3:
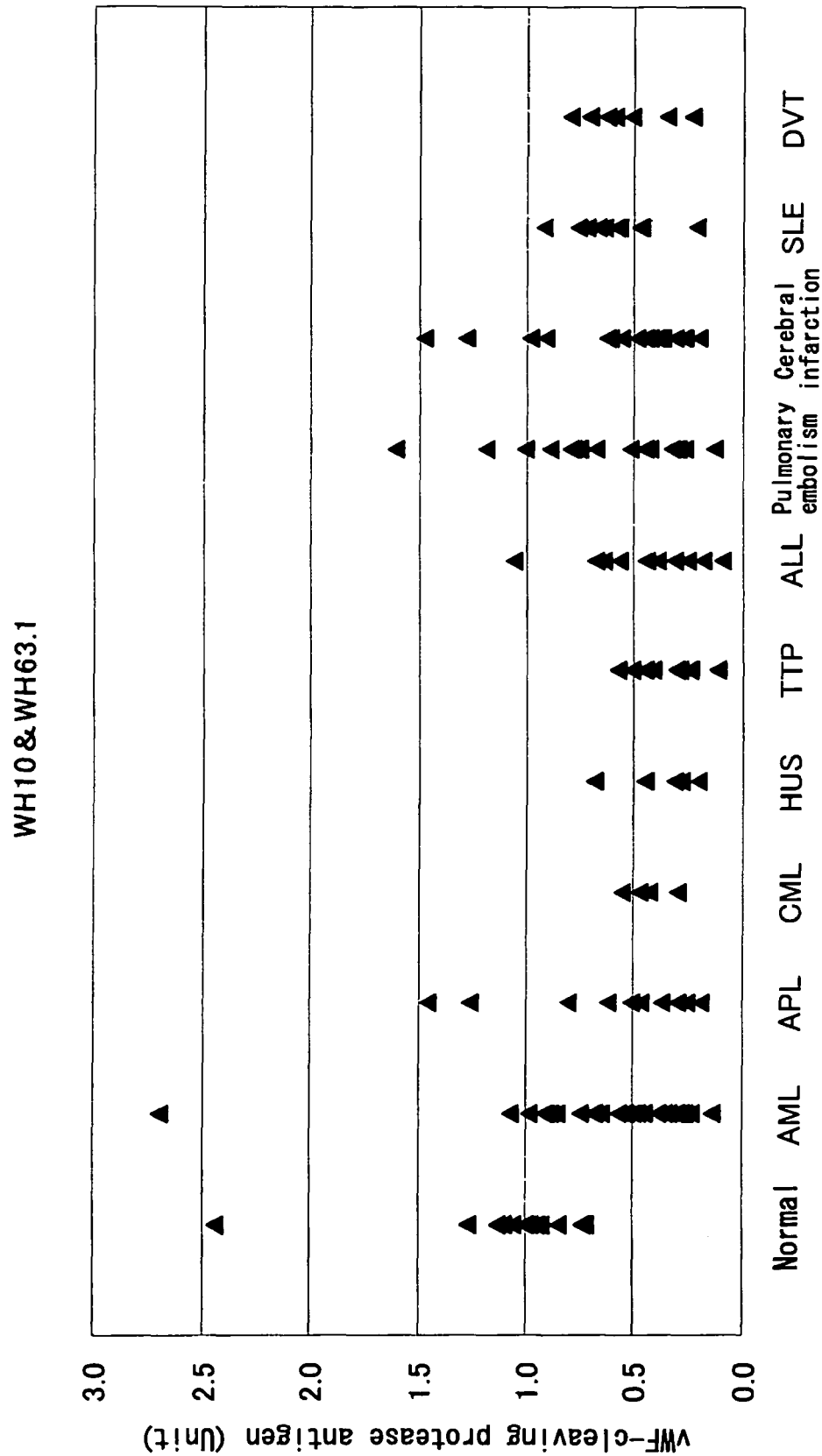
FIG. 3 is a graph showing the result obtained by comparing the amounts of vWF-cleaving protease in healthy people and patients suffering from various diseases, on the basis of the measurement using the combination of monoclonal antibodies WH10 and WH63.1 which specifically bind to the vWF-cleaving protease.
Figure 4:
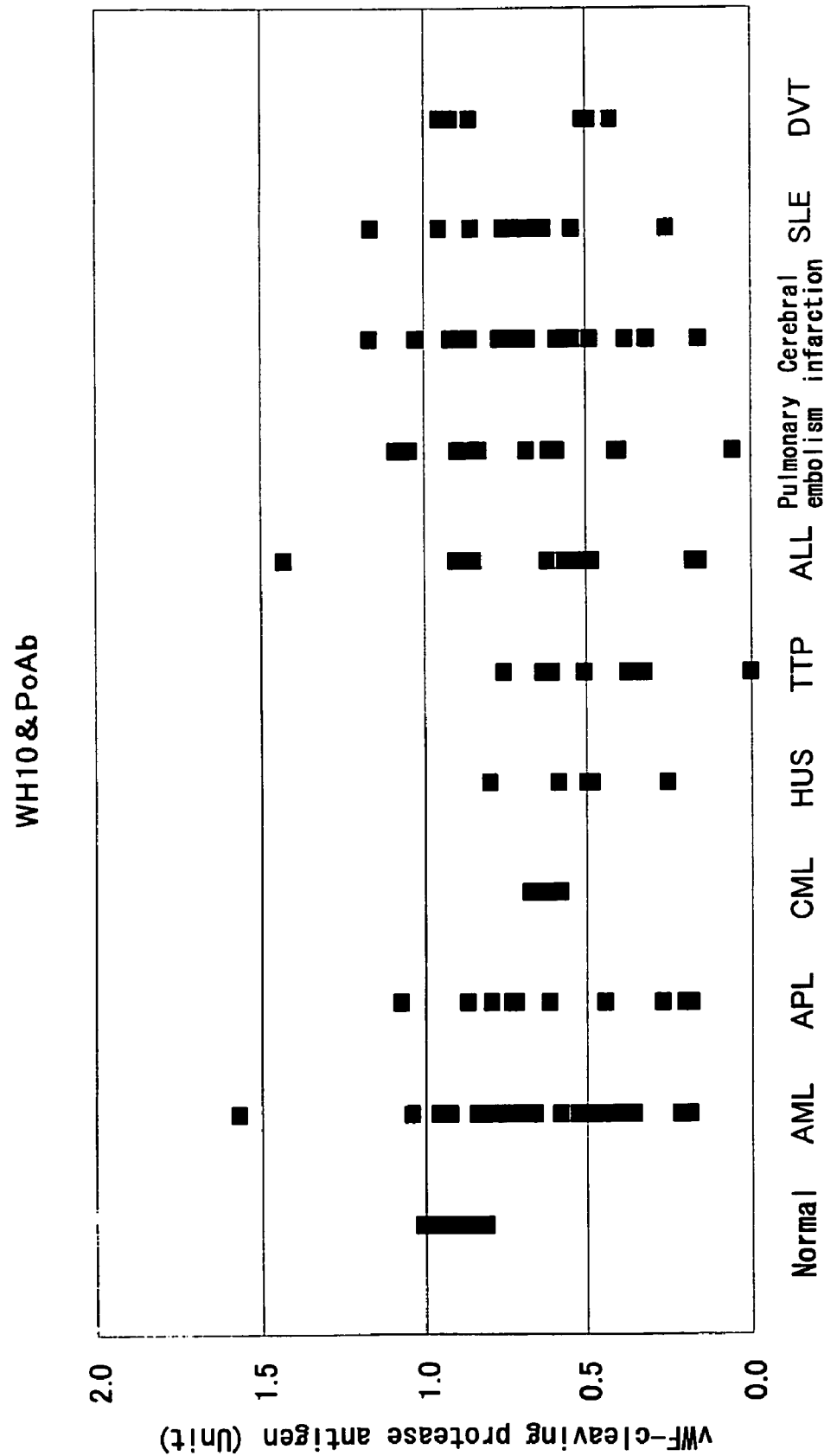
FIG. 4 is a graph showing the result obtained by comparing the amounts of vWF-cleaving protease in healthy people and patients suffering from various diseases, on the basis of the measurement using the combination of a monoclonal antibody WH10 and a polyclonal antibody which specifically bind to the vWF-cleaving protease.
Figure 5:
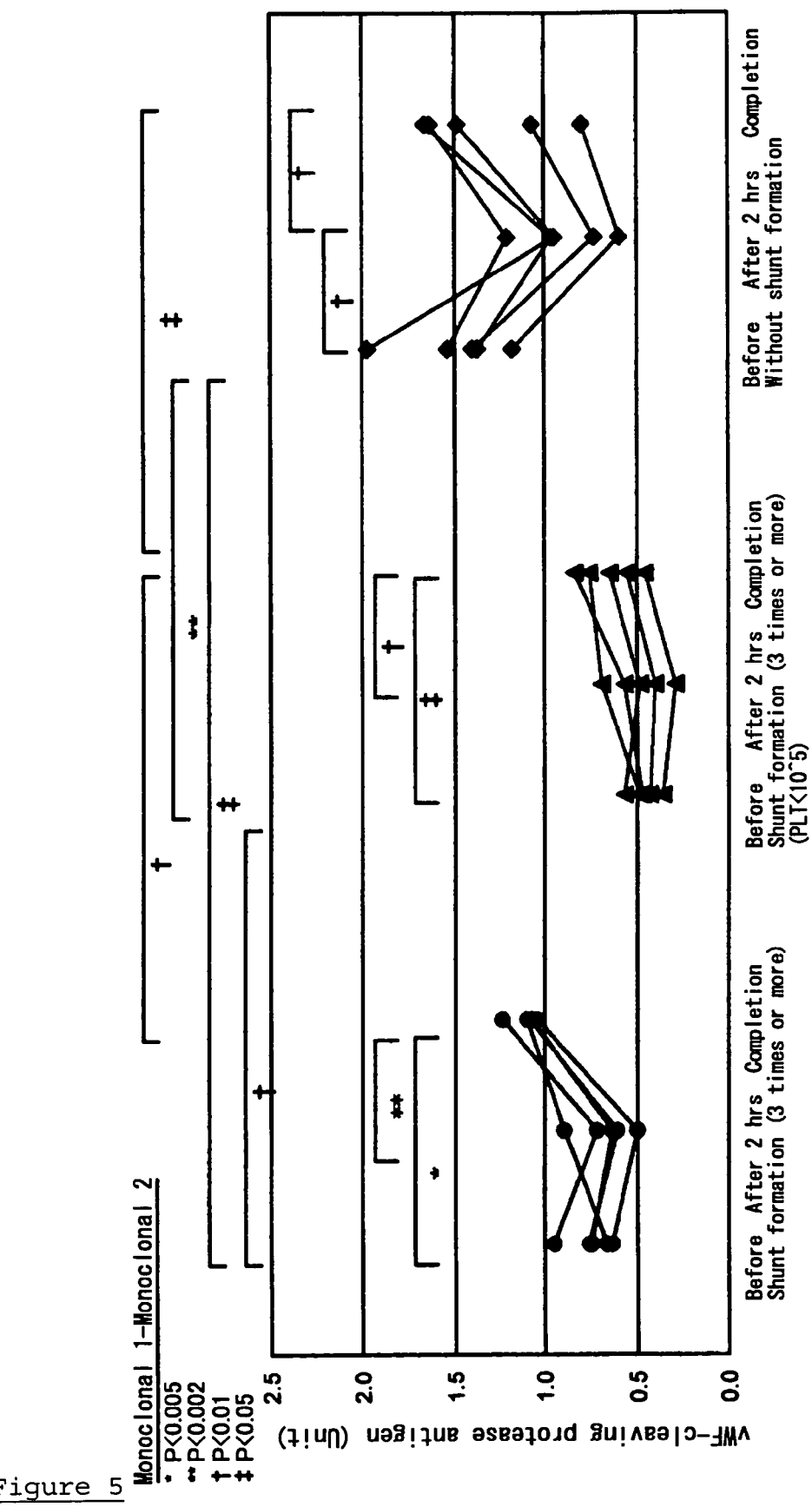
FIG. 5 is a graph showing changes of the vWF-cleaving protease before dialysis, after two hours from the beginning of dialysis, and after the completion of dialysis, in patients under a long-term treatment with dialysis with or without shunt, on the basis of the measurement using the combination of monoclonal antibodies WH10 and WH2-22-1A which specifically bind to the vWF-cleaving protease.

The invention claimed is:

1. A method of determining the severity of thrombophilia, comprising measuring a von Willebrand factor-cleaving protease from a sample of bodily fluid from a patient suffering from one or more diseases selected from the group consisting of pulmonary embolism, cerebral infarction, veno-occlusive disease, and deep vein thrombosis, wherein said bodily fluid is selected from the group consisting of whole blood, blood plasma, and serum; and correlating the quantitative level of von Willebrand factor-cleaving protease in the sample to that which would be present in a normal person, with a lower level present in the sample being indicative of an increased severity of thrombophilia;

wherein the measuring of von Willebrand factor-cleaving protease is performed by sandwich assay using at least one monoclonal antibody selected from the group consisting of WH10 accession number FERM BP-08174, WH63.1 accession number FERM BP-08175, and WH2-22-A1 accession number FERM BP-08483.

2. The method according to claim 1, wherein the severity of thrombophilia is detected in a patient under a long-term treatment with dialysis accompanied by repeated shunt.

3. A method of determining the severity of thrombophilia in a patient, comprising:

collecting a sample of bodily fluid from said patient, said bodily fluid being selected from the group consisting of whole blood, blood plasma, and serum;

analyzing said sample by sandwich immunoassay using at least one monoclonal antibody selected from the group consisting of WH10 accession number FERM BP-08174, WH63.1 accession number FERM BP-08175, and WH2-22-A1 accession number FERM BP-08483 to quantitatively obtain the level of von Willebrand factor-cleaving protease present in the sample;

correlating the quantitative level of von Willebrand factor-cleaving protease in the sample to that which would be present in a normal person, with a lower level present in the sample being indicative of an increased severity of thrombophilia, wherein the patient is suffering from one or more diseases selected from the group consisting of pulmonary embolism, cerebral infarction, veno-occlusive disease, and deep vein thrombosis.

4. The method of claim 3, where the bodily fluid is blood plasma.

5. The method of claim 3, where the patient is a person under a long-term treatment with dialysis accompanied by repeated shunts.

* * * * *

UNITED STATES PATENT AND TRADEMARK OFFICE
CERTIFICATE OF CORRECTION

| | | |
|---|---|---|
| PATENT NO. | : 8,088,624 B2 | Page 1 of 1 |
| APPLICATION NO. | : 10/584425 | |
| DATED | : January 3, 2012 | |
| INVENTOR(S) | : Ono et al. | |

It is certified that error appears in the above-identified patent and that said Letters Patent is hereby corrected as shown below:

Title page, item (54) Title, and col. 1, line 2, Delete "VON WILLENBRAND" and insert --VON WILLEBRAND--

Signed and Sealed this
Twentieth Day of March, 2012

David J. Kappos
*Director of the United States Patent and Trademark Office*

UNITED STATES PATENT AND TRADEMARK OFFICE
CERTIFICATE OF CORRECTION

PATENT NO. : 8,088,624 B2
APPLICATION NO. : 10/584425
DATED : January 3, 2012
INVENTOR(S) : Ono et al.

It is certified that error appears in the above-identified patent and that said Letters Patent is hereby corrected as shown below:

Title Page, Assignee (73): Delete "Mitsubishi Kagaku Iatron, Inc (JP)." and insert -- Mitsubishi Chemical Medience Corporation, (Japan) and Juridical Foundation The Chemo-Sero-Therapeutic Research Institute, (Japan) --

Signed and Sealed this
Twenty-ninth Day of May, 2012

David J. Kappos
*Director of the United States Patent and Trademark Office*